United States Patent [19]

Boesten et al.

[11] Patent Number: 5,874,571
[45] Date of Patent: Feb. 23, 1999

[54] PROCESS FOR THE RECOVERY OF CEPHALEXIN

[75] Inventors: Wilhelmus H. J. Boesten, Sittard; Eric C. Roos, Maastricht; Wilhelmus J. J. van den Tweel, Meerssen, all of Netherlands

[73] Assignee: Chemferm V.O.F., Breda, Netherlands

[21] Appl. No.: 903,879

[22] Filed: Jul. 31, 1997

Related U.S. Application Data

[63] Continuation of PCT/NL96/00051 Feb. 1, 1996.

[30] Foreign Application Priority Data

| | | | |
|---|---|---|---|
| Feb. 2, 1995 | [BE] | Belgium | 9500081 |
| Mar. 9, 1995 | [BE] | Belgium | 9500205 |
| Mar. 31, 1995 | [BE] | Belgium | 9500290 |

[51] Int. Cl.⁶ .......................... C12P 37/04; C07D 501/06
[52] U.S. Cl. .............................. 540/220; 435/47; 435/50; 540/215; 540/230
[58] Field of Search ..................................... 540/220, 215, 540/230; 435/47, 50

[56] References Cited

U.S. PATENT DOCUMENTS

| | | | |
|---|---|---|---|
| 3,883,519 | 5/1975 | Fujii | 260/243 C |
| 4,003,896 | 1/1977 | Faarup | 260/243 C |
| 5,470,717 | 11/1995 | Clausen . | |

FOREIGN PATENT DOCUMENTS

| | | |
|---|---|---|
| 2-164-270 | 7/1973 | France . |
| A-52-111589 | 9/1997 | Japan . |
| 93/12250 | 6/1993 | WIPO . |

*Primary Examiner*—Mukund J. Shah
*Assistant Examiner*—Pavanaram K. Sripada
*Attorney, Agent, or Firm*—Pillsbury Madison & Sutro LLP

[57] ABSTRACT

The disclosed process is for the recovery of cephalexin from a mixture containing cephalexin and 7-aminodesacetoxy cephalosporanic acid (7-ADCA), wherein a mixture of cephalexin and 7-ADCA, with a pH higher than 7, which apart from any solid cephalexin being present is homogeneous at a pH between 7 and 8.5, is subjected to a pH modification until a pH lower than 7.8 is reached, and the solid substance is recovered. The disclosed process is particularly suited for application to a reaction mixture obtained after the enzymatic acylation reaction of 7-ADCA with a phenylglycine derivative as an acylation agent. Pure cephalexin can thus be recovered in a simple manner.

15 Claims, No Drawings

PROCESS FOR THE RECOVERY OF CEPHALEXIN

PROCESS FOR THE RECOVERY OF CEPHALEXIN

This is a continuation of International Application No. PCT/NL96/00051 filed Feb. 1, 1996, which designated the U.S.

The invention relates to a process for the recovery of cephalexin from a mixture containing cephalexin and 7-aminodesacetoxy cephalosporanic acid (7-ADCA).

BACKGROUND OF THE INVENTION

In the preparation of cephalexin with 7-ADCA being acylated with a D-phenyl glycine derivative, the recovery of the cephalexin and the working up of the reaction mixture are difficult in general. Thus in WO-A-93/12250 for instance it is described that the acylation reaction never runs to completion and the ultimate purification of the final product is hindered because the acid/base properties and solubilities of certain components (in particular 7-ADCA and phenylglycine as described in U.S. Pat. No. 4,003,896) differ little from those of the final product. As a result, coprecipitation occurs, so that impure cephalexin is obtained. In WO-A-93/12250 and U.S. Pat. No. 4,003,896 the use of a complexing agent such as naphthol is proposed. However, this entails the drawback that an additional substance alien to the process has to be added.

Another method to isolate cephalexin in pure form from a mixture containing cephalexin and minor quantities of 7-ADCA is described in JP-A-52111589. According to the method described in this Japanese publication, the mixture containing 7-ADCA and cephalexin is subjected to recrystallization in an organic solvent, for instance a mixture of dichloromethane, dimethyl sulphoxide and a lower alcohol, in the presence of an alkaline component, for instance disopropyl amine. This method, too, presents the drawback that substances alien to the process have to be added. Moreover, cephalexin losses of 18% occur in this purification method.

SUMMARY AND OBJECTS OF THE INVENTION

An object of the invention is to provide a simple process which allows cephalexin to be purified without requiring use of organic substances otherwise alien to the process.

This is achieved according to the invention in that a mixture which contains cephalexin and 7-ADCA, with a pH higher than 7, which apart from any solid cephalexin being present is homogeneous at a pH between 7 and 8.5, is subjected to a pH modification till a lower pH value in the range lower than 7.8 is reached, and the solid substance present is recovered.

DETAILED DESCRIPTION OF THE INVENTION

The applicant has found that it is possible, by lowering the pH of the mixture to a value below 7.8, for instance a pH between 5 and 7.8, and more particularly a pH between 6.0 and 7.6, depending on the composition of the reaction mixture, to have cephalexin crystallize out with a purity of more than 90 mass %, and more particularly greater than 98 mass %, even if a large quantity of 7-ADCA is present in the mixture, after which the cephalexin can be recovered. In addition to cephalexin the reaction mixture often contains other valuable components, such as for instance the 7-ADCA. In order to have a commercially attractive process it is consequently important also to minimize the 7-ADCA and cephalexin losses. It has also been discovered that if the pH of the above-described reaction mixture is subsequently lowered to a value of less than 6.5, and particularly a pH between 1.5 and 5.5, 7-ADCA and the remaining cephalexin crystallize out virtually completely, after which this mixture of 7-ADCA and cephalexin can be recovered, for instance by filtration. The resulting mixture of 7-ADCA and cephalexin can optionally be re-used, so that a process is obtained which yields pure cephalexin without significant losses of 7-ADCA and cephalexin.

In a specific embodiment of the process of the present invention the pH of the mixture is first lowered until a value between 0 and 3.5, preferably between 0.5 and 2.5, is reached and subsequently it is raised until a value between 5 and 7.8, preferably between 6.0 and 7.6, is reached.

The process according to the present invention is particularly suited for use in working up of the reaction mixture which is obtained after the enzymatic acylation reaction in which 7-ADCA is acylated with D-phenylglycine amide (PGA) or esters of D-phenylglycine. Thus, the process according to the invention can, for instance be applied to a starting mixture that is obtained by successively filtering, with isolation of (immobilized) enzyme, the reaction mixture of an enzymatic acylation reaction carried out at a relatively high pH, for instance a pH between 8 and 10, and lowering the pH to a value between 7.0 and 8.5. Depending on the amount of D-phenylglycine (PG) formed during the acylation reaction, if desired, first, at a higher pH value between 7 and 8.5, —which latter pH value is chosen depending on the mixture, such that PG has been crystallized out and cephalexin has not yet—the eventually formed solid substance, which mostly will consist mainly of PG, may be isolated.

In another embodiment the starting mixture used is the mixture obtained after an enzymatic acylation reaction that ends at a relatively low pH, for instance a pH between 7 and 8.5, and after isolation of the solid substance which mainly contains the immobilized enzyme and, depending on the amount of PG formed during the acylation reaction, D-phenylglycine.

In the starting mixture containing 7-ADCA and cephalexin, a significant quantity of 7-ADCA may be present. The quantity of 7-ADCA is mostly less than 75 mol % relative to the total amount of 7-ADCA plus cephalexin, although preferably it is 2–60%, and more particularly is 5 . 50%.

The pH may be lowered in several ways in the framework of the invention, for instance, chemically by adding an acid, for instance a mineral acid, in particular sulphuric acid, hydrochloric acid or nitric acid. Another possibility is, for instance, if PGA has been used as acylation agent in the acylation reaction or if an ester of PG has been used and the pH has been kept constant by means of titration with ammonia during the acylation reaction, to lower the pH through physical removal of ammonia. Suitable physical removal methods are for instance stripping with steam or an inert gas; (steam) distillation at reduced pressure, in particular thin-film evaporation; evaporation in a spray tower; gas membrane separation or electrodialysis.

The optimum pH at which cephalexin is recovered depends on the composition of the mixture and is chosen such that optimum separation of 7-ADCA and cephalexin is achieved. In practice the optimum pH is a compromise between on the one hand high purity of the cephalexin recovered, which is achieved if the cephalexin is recovered at a relatively high pH, so that the cephalexin is still partly in solution and the 7-ADCA still completely in solution, and on the other hand a high yield, which is achieved if the pH at which the cephalexin is recovered is relatively low, so that the cephalexin has been precipitated virtually completely, while at the same time part of the 7-ADCA has also been precipitated. For the person skilled in the art it is easy to determine the optimum pH in a given situation.

The temperature at which the working up is performed is mostly lower than 35° C., preferably between 0° and 30° C., in particular between 10° and 30° C.

The process according to the invention for recovery of pure cephalexin in combination with recirculation of the mixture of 7-ADCA and cephalexin obtained after further pH lowering, applied to the mixture obtained after enzymatic acylation of 7-ADCA with PGA enables an overall high selectivity towards 7ADCA to be achieved, in particular higher than 80%. The remaining filtrate, which mainly contains minor residual amounts of PGA, may optionally be worked up further, for instance, by bringing it to a pH higher than 8, in particular between 8.5 and 10 and recovering the precipitated PGA. If desired, it is possible to apply further concentration and cooling to a temperature lower than 10° C., for instance, between 0° and 8° C. In this way a process is obtained with which both 7-ADCA and PGA can be applied with a high efficiency. In the enzymatic acylation reaction, PGA or esters of PGA for instance may be used as acylation agent.

In principle any enzyme can be used that is suitable as catalyst in the coupling reaction. Such enzymes are, for instance the enzymes that are known under the general designations 'penicillin amidase' and 'penicillin acylase'. Examples of suitable enzymes are enzymes derived from Acetobacter, Aeromonas, Alcaligenes, Aphanocladium, Bacillus sp., Cephalosporium, Escherichia, Flavobacterium, Kluyvera, Mycoplana, Protaminobacter, Pseudomonas and Xanthomonas, in particular *Acetobacter pasteurianum, Alcaligenes faecalis, Bacillus megaterium, Escherichia coli* and *Xanthomonas citrii*.

Preferably an immobilized enzyme is used because the enzyme can be easily isolated and re-used then. Immobilized enzymes are known as such and are commercially available. Examples of suitable enzymes are the *Escherichia coli* enzyme from Boehringer Mannheim GmbH, which is commercially available under the name 'Enzygel®', the immobilized Penicillin-G acylase from Recordati, the immobilized Penicilline-G acylase from Pharma Biotechnology Hannover, and an *Escherichia coli* penicilline acylase isolated as described in WO-A-92.12782 and immobilised as described in EP-A-222462.

The enzymatic acylation reaction is mostly carried out at a temperature lower than 35° C., preferably between 0° and 28° C. The pH at which the enzymatic acylation reaction is carried out is mostly between 6 and 10, and is preferably between 6.5 and 9.

In practice the enzymatic acylation reaction and the working up of the reaction mixture are mostly carried out in water. Optionally, the reaction mixture may also contain an organic solvent or a mixture of organic solvents, preferably less than 30 vol. %. Examples of organic solvents that can be used are alcohols with 1–7 carbon atoms such as, for instance, a monoalcohol, in particular methanol or ethanol; a diol, in particular ethylene glycol or a triol, in particular glycerol.

In the framework of the present invention the various components may be present in the reaction mixture in the free form or as salts. The pH values mentioned are in all cases the pH values measured at room temperature.

The invention will be further elucidated by means of the following examples, without however being restricted thereto.

ABBREVIATIONS

CEX=cephalexin
CEX.H$_2$O=cephalexin monohydrate
7-ADCA=7-aminodesacetoxy cephalosporanic acid
PGA=D-phenylglycine amide
PG=D-phenylglycine

EXAMPLE I

Working up of a mixture obtained after enzymatic coupling of 550 mM of PGA.½h$_2$SO$_4$ with 410 mM of 7-ADCA at 5° C.

A mixture of 80 g of PGA.½H$_2$SO$_4$, 64.2 g of 7-ADCA and 425 ml of water was cooled to 5° C., after which the pH was brought to 7.6 with 25 ml of 25 wt. % aqueous NH$_4$OH. The resulting suspension (the 'feed') was added to 190 g of wet immobilized Penicilline-G acylase from Recordati (Milan). This enzyme is commercially available in a mixture of water and glycerol ('wet enzyme'); before use it was washed three times with 100 ml of water.

After stirring for two hours (the pH had now risen to 8.35) the reaction mixture was filtered through a G-3 glass filter; the residue was washed two times with 50 ml of water. This residue was a mixture of enzyme and PG formed during the reaction.

The filtrate (a yellow solution) was cautiously acidified now to pH=7.2 with concentrated sulphuric acid (total 4 ml). After 30 minutes, filtering, washing with 3×30 ml of water and drying were performed, which yielded 40.8 g of CEX.H$_2$O with a chemical purity (on a water-free basis) of >99.5%.

The mother liquor of the CEX crystallization was again acidified to pH=4.0 with concentrated sulphuric acid (total 3.7 ml). After stirring for 17 hours, filtering and washing with 3×20 ml of water were performed, which yielded 30.2 g of solid substance, calculated on a water-free basis. This solid substance contained a mixture of CEX and 7-ADCA in a molar ratio of 60:40.

EXAMPLE II

Enzymatic coupling of 500 mM of PGA and 500 mM of 7-ADCA at 5° C., followed by working up.

A feed consisting of 75.0 g of free PGA, 109.2 g of 7-ADCA, 10.0 g of PG and 750 ml of water was cooled to 5° C. and was then added to 150 g of wet enzyme Penicilline-G acylase from Recordati (Milaan) (which had first been washed). After stirring for 2 hours and 10 minutes at 5° C. the mixture was filtered (through a G-3 glass filter) and washed with 1×100 ml of water.

The resulting filtrate contained the following components:
CEX=328 mmol
7-ADCA=161 mmol
PG=75 mmol
PGA=46 mmol The conversion relative to 7-ADCA thus amounted to 66%. This mixture was worked up as follows: by means of a rotary film evaporator, 360 ml of the total mixture (971.4 g) was distilled off at 20° C. (in about 45–60 minutes), after which 360 ml of fresh water was added. This procedure was repeated one time. The resulting suspension was filtered through a G-3 glass filter; the residue was rewashed with cold water (1×50 ml) and acetone (2×30 ml) and subsequently dried for one night. Yield: 57.0 g of white substance; the CEX content on a water-free basis was >99%. The filtrate from the CEX filtration (incl. washing waters) was then cooled again to 5° C. and acidified to pH=4.5 by means of 12N aqueous $H_2SO_4$. After stirring for 2 hours the suspension was filtered through a G-3 glass filter. Yield: 78.4 g of light yellow substance (calculated on a water-free basis); this substance contained a mixture of CEX and 7-ADCA in a molar ratio of 75:25.

What is claimed is:

1. A process for the recovery of cephalexin from a mixture containing cephalexin and 7-aminodesacetoxy cephalosporanic acid (7-ADCA comprising:

subjecting a starting mixture which contains cephalexin and 7-ADCA, with a pH higher than 7, which apart from any solid cephalexin being present is homogeneous at a pH between 7 and 8.5, to a pH modification till a lower pH with a value between 5 and 7.8 is reached; and recovering the solid substance present said solid substance comprising cephalexin.

2. A process according to claim 1, wherein the pH is lowered to a value between 6 and 7.6.

3. A process for recovering substances from a mixture containing cephalexin and 7-aminodesacetoxy cephalosporanic acid (7-ADCA) comprising:

reducing the pH of a mixture containing cephalexin and 7-ADCA having a pH greater than 7, said mixture being homogeneous at a pH between 7 and 8.5 apart from any solid cephalexin present, to a pH value between 0 and 3.5; raising the pH until a pH value between 6 and 7.6 is reached; and recovering, as a solid substance, cephalexin.

4. A process according to claim 3, wherein the pH is first lowered until a value between 0.5 and 2.5 is reached.

5. A process according to claims 1 or 2, wherein the starting mixture contains 2–60 mol % of 7-ADCA, calculated relative to the total amount of 7-ADCA and cephalexin.

6. A process according to claims 1 or 2, wherein said process further comprises reducing of pH of the liquid phase remaining after recovery of the solid substance to a pH lower than 6.5 and recovering a further solid substance, said further solid substance comprising 7-ADCA or a combination of 7-ADCA and cephalexin.

7. A process according to claim 6, wherein the pH of the remaining liquid phase is lowered to a pH between 1.5 and 5.5.

8. A process according to claim 1 or 2, wherein the starting mixture of cephalexin and 7-ADCA is prepared by: lowering the pH of a reaction mixture following an enzymatic acylation reaction carried out at a pH between 8 and 10 to a pH value between 7.0 and 8.5, separating out a solid substance present after the enzymatic acylation reaction, and optionally further lowering the pH to a value between 7.0 and 8.5, whereby said starting mixture is obtained.

9. A process according to claim 8, wherein, in preparing said starting mixture, said solid substance separated out after the enzymatic acylation reaction comprises the enzyme.

10. A process according to claims 1 or 2, wherein said starting mixture of cephalexin and 7-ADCA is obtained from the reaction mixture of an enzyme catalyzed acylation reaction at a pH between 7 and 8.5, from which a solid substance present after the enzyme catalyzed acylation reaction, has been isolated.

11. A process according to claim 5, wherein a remaining liquid phase from said recovering is subjected to a pH reduction to a value less than 6.5, and a further solid substance is recovered.

12. A process according to claim 5, wherein said starting mixture contains 5–50 mol % 7-ADCA.

13. A process according to claim 8, wherein after the separating the pH is lowered to a lower value between 7.0 and 8.5.

14. A process according to claim 8, wherein said enzyme is an immobilized enzyme.

15. A process according to claim 11, wherein said remaining liquid phase is subjected to a pH reduction to a value between 1.5 and 5.5.

* * * * *